(12) United States Patent
Che et al.

(10) Patent No.: US 11,505,656 B2
(45) Date of Patent: Nov. 22, 2022

(54) METHOD FOR EMBEDDING A LOAD BASED ON GEL HIGH HYDROSTATIC PRESSURE LIQUEFACTION

(71) Applicant: XIAMEN UNIVERSITY, Xiamen (CN)

(72) Inventors: Liming Che, Xiamen (CN); Xiang Li, Xiamen (CN); Ning He, Xiamen (CN); Xue'e Wu, Xiamen (CN); Yuanpeng Wang, Xiamen (CN); Xueping Ling, Xiamen (CN)

(73) Assignee: XIAMEN UNIVERSITY, Xiamen (CN)

( * ) Notice: Subject to any disclaimer, the term of this patent is extended or adjusted under 35 U.S.C. 154(b) by 902 days.

(21) Appl. No.: 16/374,464

(22) Filed: Apr. 3, 2019

(65) Prior Publication Data

US 2020/0239646 A1 Jul. 30, 2020

(30) Foreign Application Priority Data

Jan. 24, 2019 (CN) .................. CN201910068715

(51) Int. Cl.
| | | |
|---|---|---|
| *C08J 3/075* | (2006.01) | |
| *A61L 27/52* | (2006.01) | |
| *A61L 27/20* | (2006.01) | |
| *A61K 47/36* | (2006.01) | |
| *A61K 31/353* | (2006.01) | |
| *A61K 38/38* | (2006.01) | |
| *A61K 31/375* | (2006.01) | |
| *A61K 35/747* | (2015.01) | |
| *A61K 35/00* | (2006.01) | |

(52) U.S. Cl.
CPC ............. *C08J 3/075* (2013.01); *A61K 31/353* (2013.01); *A61K 31/375* (2013.01); *A61K 35/747* (2013.01); *A61K 38/385* (2013.01); *A61K 47/36* (2013.01); *A61L 27/20* (2013.01); *A61L 27/52* (2013.01); *A61K 2035/115* (2013.01); *C08J 2305/06* (2013.01)

(58) Field of Classification Search
CPC ....... C08J 3/075; C08J 2305/06; A61K 47/36; A61L 27/52
See application file for complete search history.

*Primary Examiner* — Lynn Y Fan
(74) *Attorney, Agent, or Firm* — Cooper Legal Group LLC

(57) ABSTRACT

The invention relates to a method for embedding a load based on gel high hydrostatic pressure liquefaction. Using the phenomenon that the physical gel is liquefied under high pressure, the vacuum-packaged high-methoxyl pectin gel is treated under a pressure of 400-600 MPa for 5-30 min, mixed with the load, and then subjected to a pressure of 400-600 MPa for homogenization treatment for 5 to 30 min. After pressure relief, the liquefied gel is poured into a mold for reshaping, followed by removal of free water and coating treatment. This method combines the advantages of high hydrostatic pressure technology in modification and sterilization. It has mild embedding conditions and wide sources of raw materials to prepare the carrier, which has excellent biocompatibility and biodegradability. It can be widely used for embedding microorganisms, enzymes, proteins and small molecular substances. The loaded gel prepared by the method has high microbial safety, can effectively maintain the activity of the load. The load distribution is uniform, and the load amount is much larger than the traditional adsorption load.

10 Claims, 2 Drawing Sheets

METHOD FOR EMBEDDING A LOAD BASED ON GEL HIGH HYDROSTATIC PRESSURE LIQUEFACTION

TECHNICAL FIELD

The present disclosure belongs to the field of immobilized biology, in particular relates to a preparation method for hydrogel, which is suitable for an encapsulating treatment, specifically to a method for encapsulating a load based on melting of pectin gel under high hydrostatic pressure.

BACKGROUND TECHNOLOGY

Food high hydrostatic pressure technology is a non-thermal food processing method that uses pressure of 100 to 1000 MPa to treat food at room temperature or mild heating conditions. Initially, high hydrostatic pressure technology was often used to inactivate pathogenic bacteria, spoilage bacteria, yeasts, molds, viruses and spores in food. In practical food processing applications, non-covalent bonds (including ionic bonds, hydrogen bonds and hydrophobic interactions) that maintain the multilevel structure of macromolecules increase or decrease under high pressure, resulting in structural changes of macromolecules (such as carbohydrates and proteins) in food, thus changing some physicochemical properties of food.

Hydrogel is a water-swelling hydrophilic polymer network, which can swell in water and maintain a large amount of water, while maintaining a three-dimensional network structure. According to the different ways of network bonding, hydrogels can be divided into physical gels and chemical gels. Physical gels are formed through physical forces such as electrostatic interaction, hydrogen bonds, chain entanglement, etc. This gel is not permanent, and can be changed to sol at certain pressure, and then it can restore the gel state after pressure relief. Chemical gels are a three-dimensional network polymer formed by chemical bond, which is permanent and insensitive to pressure. Hydrogels have been widely used in food, medicine and biomaterials industries because of their stability, solubility, half-life and bioavailability. Traditional hydrogels are usually prepared from synthetic materials, and they have been successfully used as oral drug delivery systems. However, these synthetic-based hydrogels are inherently limited in food applications because their ingredients are generally not acceptable to food health advocate. Pectin is a kind of macromolecule carbohydrate widely existing in the cell wall of green plants. It is the main component that affects the physical properties (such as texture, rheology and turbidity stability) of fruits and fruit products. Due to its diversity of gel mechanisms and excellent biocompatibility, pectin is of great potential value in biomedical fields such as drug delivery, gene delivery, wound healing and tissue engineering.

SUMMARY OF THE PRESENT DISCLOSURE

The objective of the present disclosure is to provide a method for encapsulating a load based on melting of pectin gel under high hydrostatic pressure, which comprises the following steps:

(1) preparation of pectin gel: a certain amount of high-methoxyl pectin (high-methoxyl pectin, preferred food grade) is dissolved in distilled water, stirred at room temperature for 8-12 h and then placed in a water bath at 80-90° C., after the temperature is stabilized, a certain amount of soluble solids is added, after fully stirred, the mixed liquid was poured into soft food packages, vacuum-packaged and fully cooled (preferably stored in a refrigerator at 4° C. for 1-3 days); the mass concentrations of high-methoxyl pectin and soluble solids in the mixture are 0.5-2% and 50-70% respectively;

(2) integrated treatment of melting of pectin gel under high hydrostatic pressure and sterilization: the vacuum-packaged gel in step (1) is placed in the pressure vessel filled with liquid pressure transmitting medium (preferably water) and treated at the pressure of 400-600 MPa for 5-30 min;

(3) encapsulating of the load: after high pressure treatment, the pectin gel is converted into a sol state, and the load and the sol is mixed and fully stirred; the operation was completed within 10 to 20 min after pressure relief;

(4) the mixture thoroughly stirred in step (3) is poured into a soft package and vacuum-packaged; the package of the vacuum-packaged mixture is placed in the pressure vessel filled with liquid pressure transmitting medium and treated at the pressure of 400-600 MPa for 5-30 min. After pressure relief, the mixture is quickly poured into the mold and formed at suitable temperature for 1-3 days;

or, the mixture of the loaded material and the sol after being fully stirred in step (3) is directly poured into the mold for forming;

(5) removal of the free water: the formed gel prepared by step (4) is dried to constant weight at suitable temperature;

(6) coating of the gel: Solution A: a certain amount of low-methoxyl pectin (low-methoxyl pectin, preferred food grade) is dissolved in distilled water, stirred for 8-12 h at room temperature, and the pH (preferred 0.05 g/ml of NaOH solution) is adjusted, the final mass concentration of low-methoxyl pectin is 2-5%, and the final pH of solution is 8-12; Solution B: a certain amount of soluble calcium salt (preferably anhydrous calcium chloride) is weighted, dissolved in distilled water and made up to a volume, and a calcium salt solution with a Ca2+ concentration of 1 to 5 mmol/L is obtained; the dry gel prepared by step (5) is infiltrated in Solution B and transferred rapidly to Solution A, and then rapidly transferred from Solution A to Solution B, then a low-methoxyl pectin gel membrane is attached to the gel surface, and the coating operation is repeated 1-2 times.

The high-methoxyl pectin mentioned in the step (1) can be derived from apples, citrus, grapefruit, lemon, etc. The degree of methoxylation is 50-80%, and the mass concentration is 0.5-2%.

The soluble solids mentioned in the step (1) are generally sucrose, which can be replaced by fructose and glucose. The percentage of the soluble solids added in the step (1) is 50-70% of the total mass.

In the steps (2) and (4), the high hydrostatic pressure treatment pressure is 400-600 MPa, the holding time is 5-30 min, and the treatment temperature is room temperature.

The loads mentioned in step (3) include at least one of microorganisms, enzymes, proteins and small molecular substances.

The high hydrostatic pressure homogenization treatment mentioned in step (4) is only used for encapsulating small molecular substances, but cannot be carried out for encapsulating microorganisms and macromolecular substances. Instead, the mixture of load substances and sol mentioned in step (3) should be directly poured into the mold for forming.

The "suitable temperature" mentioned in the steps (4) and (5) refers to the optimum temperature for maintaining the activity of the loaded substance and preferably the room temperature.

The coating operation mentioned in step 6 is intended to prevent rapid dissolution of high-methoxyl pectin gels in water. Because the gel structure of high-methoxyl pectin is maintained by intermolecular hydrogen bonds and hydrophobic bonds which are dissolvable, the high-methoxyl pectin gel is wrapped with an insoluble gel to give it a better structural strength in this present disclosure. The degree of methoxylation of the low-methoxyl pectin in solution A is 10-30%, the mass concentration is 2-5%, and the pH is 8-12. The concentration of $Ca^{2+}$ in solution B is 1 to 5 mmol/L; the coating operation is repeated 1-2 times.

Another objective of the present disclosure is to provide a loaded gel, which is prepared by the aforementioned method.

Compared with the existing process technology, the present disclosure has the following advantages:

(1) Pectin is a natural polysaccharide with abundant sources which has excellent biocompatibility and biodegradability. The degradation products are beneficial and harmless to human body. Numerous studies have confirmed that pectin has the functions of lowering blood sugar and blood fat, reducing cholesterol, clearing blood vessels and other health functions.

(2) This method combines the advantages of high hydrostatic pressure technology in two aspects of modification and sterilization, which not only realizes the melting of pectin gels under high hydrostatic pressure, but also improves the microbiological safety of gels.

(3) The encapsulating process of the load is mild, and the destruction of the activity of the load by the high temperature is avoided. The gels have different gel strength after treatment at different pressure, thereby the regulation of the gel structure can be realized by adjusting the high pressure treatment conditions, and the release rate of the load can be controlled.

(4) The method can be widely used for the encapsulating of microorganisms, enzymes, proteins and small molecular substances. The load is uniform and the load amount is much larger than the traditional adsorption load.

DRAWINGS

DETAILED DESCRIPTION

Figure 1:
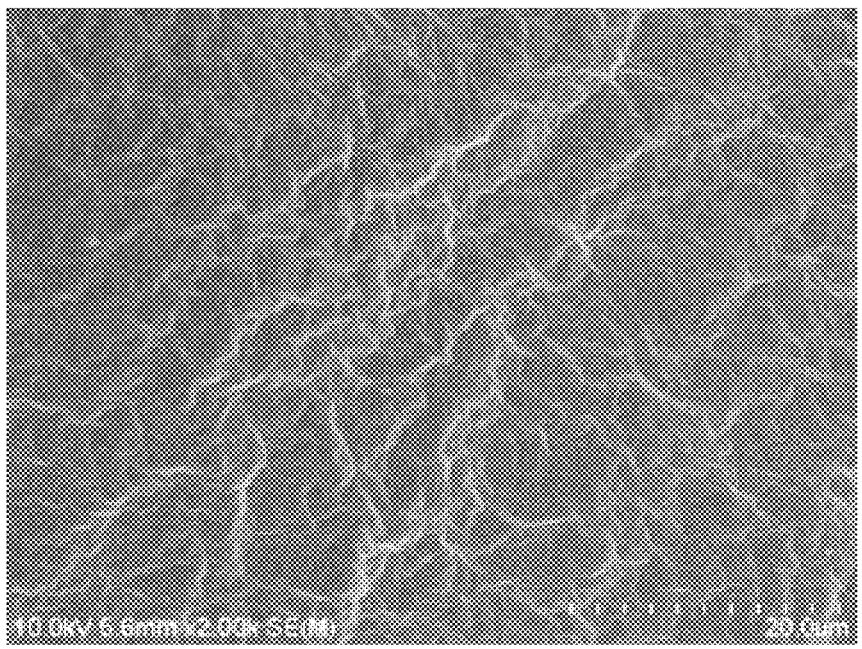
FIG. 1 is the section morphology of the high-methoxyl apple pectin gel without high hydrostatic pressure treatment.
Figure 2:
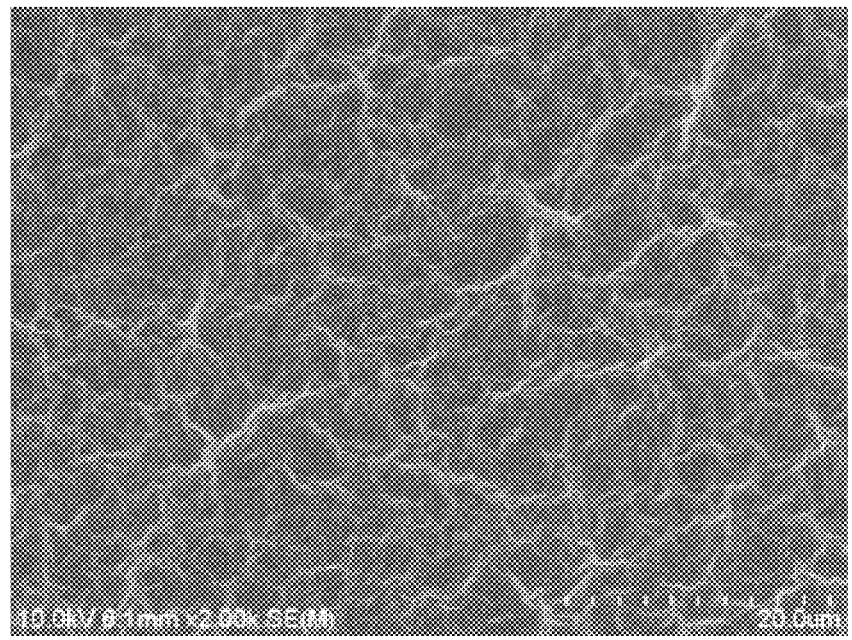
FIG. 2 is the section morphology of the high-methoxyl apple pectin gel after treatment at 400 MPa.
Figure 3:
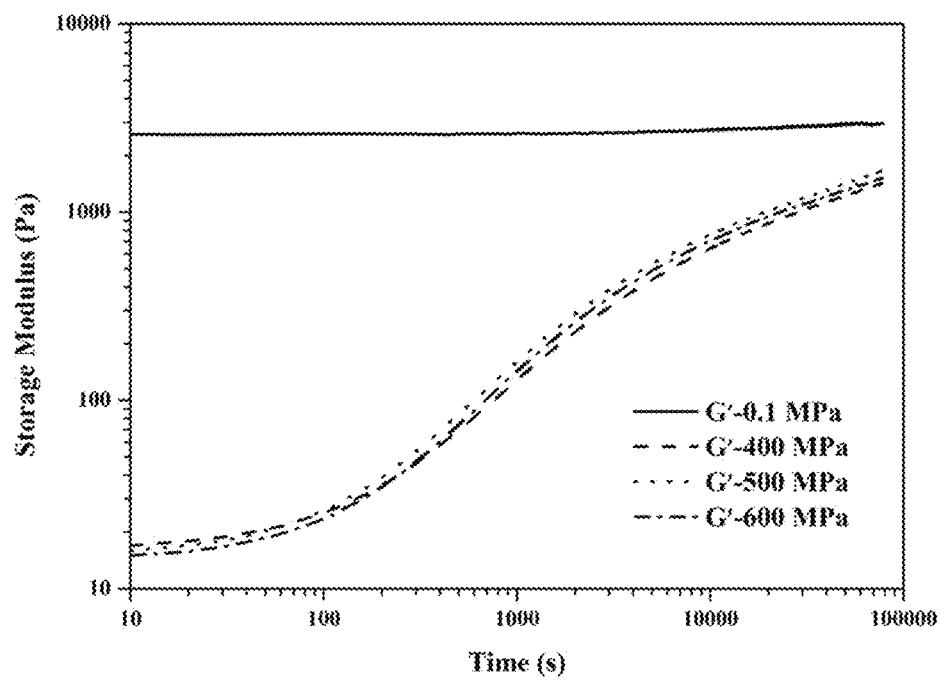
FIG. 3 is the sol-gel transition kinetics curve of high-methoxyl apple pectin after treatment at different pressures.

The following is further explained with specific embodiments. It should be understood that these embodiments are used only to illustrate the present disclosure and not to limit the scope of application of the present disclosure. In addition, after reading the contents of the present disclosure, skilled personnel in the field may make various modifications to the present disclosure, which fall within the scope of claims attached to this application.

Embodiment 1

A method for encapsulating *Lactobacillus acidophilus* based on melting of pectin gel under high hydrostatic pressure, which comprises the following steps:

(1) preparation of pectin gel: 3 g of high-methoxyl pectin (from apple, the degree of methoxylation of 66%) was weighed in a beaker, and 117 g of distilled water was added, then stirred at room temperature for 12 h, dissolved thoroughly, placed in a water bath at 90° C., 180 g of glucose was added after the temperature is stable, after stirring and dissolving, the water lost by evaporation was replenished, the mixture was poured into a soft food package while hot, and stored it in a refrigerator at 4° C. for 30 h after vacuum packaging to obtain a pectin gel;

(2) integrated treatment of melting of pectin gel under high hydrostatic pressure and sterilization: the vacuum-packaged gel in step (1) was placed in the pressure vessel filled with water and treated at 600 MPa for 5 min, and then the pectin sol was obtained after pressure relief;

(3) encapsulating of *Lactobacillus acidophilus*: 1 ml of the bacterial suspension (100 cfu/ml, containing the nitrogen source, inorganic elements and growth factors necessary for the growth of *Lactobacillus acidophilus*) and the sol obtained in the step (2) were mixed for 10 min after pressure relief, and thoroughly stirred, then poured into a mold and stored at 37° C. for 72 h;

(4) coating of the gel: Solution A: 5 g of low-methoxyl pectin (from apple, the degree of methoxylation of 14%) was dissolved in distilled water, stirred at room temperature for 8 h, pH was adjusted with 0.05 g/ml NaOH solution, the final mass concentration of low-methoxyl pectin was 5%, and the final pH of the solution was 9; Solution B: 5 g of anhydrous calcium chloride was weighed and diluted to 100 ml with distilled water to obtain a calcium chloride solution of 0.05 g/ml; the shaped gel prepared in the step (3) was infiltrated in the solution B and rapidly transferred to the solution A, and then rapidly transferred from the solution A to the solution B, and repeated twice.

The loaded gel prepared in this embodiment can culture *Lactobacillus acidophilus* while fixing it, and the glucose in the gel provides a natural carbon source for the growth of *Lactobacillus acidophilus*. The encapsulating conditions are mild to effectively maintain the activity of *Lactobacillus acidophilus* and a high cell density (269 cfu/g) can be obtained; in addition, the gel can carry the *Lactobacillus acidophilus* to the gastrointestinal tract smoothly, thereby exerting its biological effects.

Embodiment 2

A method for encapsulating proanthocyanidins based on melting of pectin gel under high hydrostatic pressure includes the following steps:

(1) preparation of pectin gel: 6 g of high-methoxyl pectin (from citrus, the degree of methoxylation of 69%) was weighted in a beaker, 144 g of distilled water was added, stirred at room temperature for 8 h, dissolved thoroughly, placed in a water bath at 80° C., 150 g of sucrose was added after temperature stabilization, after stirring and dissolving, the water lost by evaporation was replenished, the mixture was poured into a soft food package while hot, and stored it in a refrigerator at 4° C. for 24 h after vacuum packaging to obtain a pectin gel;

(2) integrated treatment of melting of pectin gel under high hydrostatic pressure and sterilization: the vacuum-packaged gel in step (1) was placed in the pressure vessel filled with water and treated at 400 MPa for 20 min, and then the pectin sol is obtained after pressure relief;

(3) encapsulating of proanthocyanidins: the proanthocyanidin powder was mixed with the sol obtained in step (2)

within 10 min after pressure relief, then fully stirred and poured into the soft food package for vacuum packaging;

(4) high hydrostatic pressure homogenization treatment: the vacuum-packaged mixture in step (3) was placed in a pressure vessel and treated at 600 MPa for 5 min After pressure relief, the mixture was quickly poured into the mold and formed in a refrigerator at 4° C. for 24 h;

(5) removal of the free water: the gel prepared in step (4) was placed in a desiccator and dried at room temperature for 8 h;

(6) coating of the gel: Solution A: 4 g of low-methoxyl pectin (from citrus, the degree of methoxylation of 29%) was dissolved in distilled water, stirred at room temperature for 12 h, pH was adjusted with 0.05 g/ml NaOH solution, the final mass concentration of low-methoxyl pectin was 4%, and the final pH of the solution was 12; Solution B: 4 g of anhydrous calcium chloride was weighed and diluted to 100 ml with distilled water to obtain a calcium chloride solution of 0.04 g/ml; the dry gel prepared by step (5) was infiltrated in Solution B and transferred rapidly to Solution A, and then transferred rapidly from Solution A to Solution B, and repeated twice.

Figure 4:
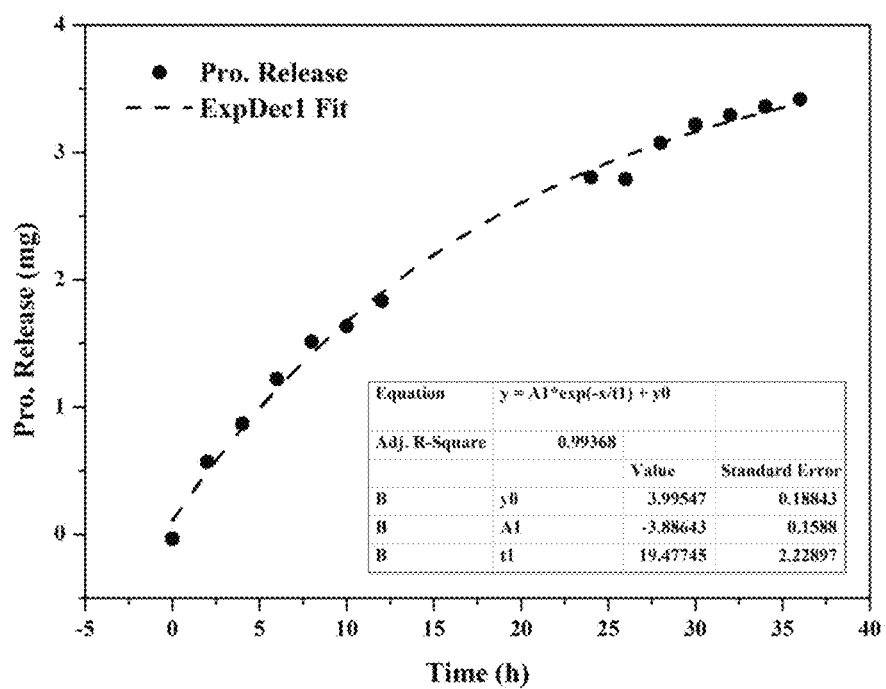
FIG. 4 is a release kinetic curve of procyanidins from a loaded gel prepared according to the steps described in embodiment 2.

The loaded gel prepared in this embodiment can effectively prevent oxidation of proanthocyanidins, and the proanthocyanidins in the gel can be slowly diffused after administration to facilitate absorption by the human body. The release kinetics curve of proanthocyanidins from the loaded gel prepared by this step is shown in FIG. 4. The release conditions are as follows:

(1) the gel mass was 4 g, and the gel shape into a cylinder that was 25 mm in diameter and 5 mm in height;

(2) the release environment was 100 ml deionized water, the release temperature was 37° C., and the shaker speed is 100 rpm.

Embodiment 3

A method for encapsulating bovine serum albumin (BSA) based on melting of pectin gel under high hydrostatic pressure includes the following steps:

(1) preparation of pectin gel: 4.5 g high-methoxyl pectin (from apple, the degree of methoxylation of 79%) was weighed in beaker, 130.5 g distilled water was added, stirred for 10 h at room temperature, fully dissolved and put in a water bath at 85° C., after the temperature is stable, 165 g soluble solids were added, after stirring and dissolving, the water lost by evaporation was added, the mixture was poured into a soft food package while hot, and stored in a refrigerator at 4° C. for 48 h, and then the pectin gel was obtained;

(2) integrated treatment of melting of pectin gel under high hydrostatic pressure and sterilization: the vacuum-packaged gel in step (1) was placed in the pressure vessel filled with water and treated at 500 MPa for 30 min, and then the pectin sol was obtained after pressure relief;

(3) encapsulating of BSA: the BSA powder was mixed with the sol obtained in step (2) within 15 min after pressure relief, fully stirred, and poured into the mold, and stored at 4° C. for 48 h for forming;

(4) removal of the free water: the gel prepared in step (3) was placed in a desiccator and dried at room temperature for 12 h;

(5) coating of the gel: Solution A: 3 g of low-methoxyl pectin (from grapefruit, the degree of methoxylation of 25%) was dissolved in distilled water, stirred at room temperature for 12 h, and pH was adjusted with 0.05 g/ml NaOH solution, the final mass concentration of low-methoxyl pectin was 3%, and the final pH of the solution was 11; Solution B: 3 g of anhydrous calcium chloride was weighed and diluted to 100 ml with distilled water to obtain a calcium chloride solution of 0.03 g/ml; the dry gel prepared by step (4) was infiltrated in Solution B and transferred rapidly to Solution A, and then rapidly transferred from Solution A to Solution B.

Because of the hydrogen bond interaction between high-methoxyl pectin and BSA, the binding effect of carrier on drug molecules is enhanced and the release rate of BSA is reduced.

Embodiment 4

A method for encapsulating vitamin C by melting of pectin gel under high hydrostatic pressure includes the following steps:

(1) preparation of pectin gel: 6 g of high-methoxyl pectin (from citrus, the degree of methoxylation of 71%) was weighed in a beaker, 114 g of distilled water was added, stirred at room temperature for 9 h, dissolved well, placed in a water bath at 80° C., 180 g of soluble solids was added after the temperature is stable, after stirring and dissolving, the water lost by evaporation was replenished, the mixture was poured into a soft food package while hot, and stored it in a refrigerator at 4° C. for 32 h after vacuum packaging to obtain the pectin gel;

(2) integrated treatment of melting of pectin gel under high hydrostatic pressure and sterilization: the vacuum-packaged gel in step (1) was placed in the pressure vessel filled with water and treated at 550 MPa for 15 min, and then the pectin sol was obtained after pressure relief;

(3) encapsulating of vitamin C: the vitamin C powder was mixed with the sol obtained in step (2) within 10 min after pressure relief, fully stirred and poured into the soft food package for vacuum packaging;

(4) high hydrostatic pressure homogenization treatment: the vacuum-packaged mixture in step (3) was placed in a pressure vessel and treated at 500 MPa for 15 min After pressure relief, the mixture was quickly poured into the mold and formed in a refrigerator at 4° C. for 32 h;

(5) removal of the free water: the gel prepared in step (4) was placed in a desiccator and dried at room temperature for 24 h;

(6) coating of the gel: Solution A: 4.5 g of low-methoxyl pectin (from lemon, the degree of methoxylation of 21%) was dissolved in distilled water, stirred at room temperature for 12 h, pH 12 was adjusted with 0.05 g/ml NaOH solution, the final mass concentration of low-methoxyl pectin was 4.5%, and the final pH of the solution was 10; Solution B: 3.5 g of anhydrous calcium chloride was weighed and diluted to 100 ml with distilled water to obtain a calcium chloride solution of 0.35 g/ml; the dry gel prepared by step (5) was infiltrated in Solution B and transferred rapidly to Solution A, and then transferred rapidly from Solution A to Solution B, and repeated twice.

The present disclosure combines the advantages of high hydrostatic pressure sterilization and modification, and the prepared gel has good microbiological safety. Its raw materials are widely used, and the encapsulating operation can be carried out at room temperature, which retains the biological activity of the carrier. The method can be widely used for encapsulating microorganisms, enzymes, proteins and small molecular substances. The load distribution is uniform and the load amount is much larger than the traditional adsorption load.

The invention claimed is:

1. A method for encapsulating a load based on melting of pectin gel under high hydrostatic pressure, comprising the following steps:
   (1) dissolving a first pectin gel in distilled water, stirring at room temperature for 8-12 hours, and then placing in a water bath at 80-90° C., after a temperature of the first pectin gel is stable, adding soluble solid stirring to obtain a mixed solution, then pouring the mixed solution into a first package, hermetically packaging in vacuum, and cooling to obtain a vacuum-packaged pectin gel, wherein mass concentrations of the first pectin gel and the soluble solid in the mixed solution are respectively 0.5-2% and 50-70%;
   (2) placing the vacuum-packaged pectin gel in a first pressure vessel filled with pressure transmitting liquid, and treating at a pressure of 400-600 MPa for 5-30 minutes;
   (3) converting the vacuum-packaged pectin gel into a sol, mixing the load and the sol, and stirring to obtain a mixture, wherein the mixing and the stirring in step 3 are complete within 10 to 20 minutes after the pressure in step 2 is released;
   (4) pouring the mixture into a mold to obtain a formed pectin gel;
   (5) drying the formed pectin gel to a constant weight to obtain a dried pectin gel;
   (6) dissolving a second pectin gel in distilled water, stirring at room temperature to obtain a solution A for 8 to 12 hours, and adjusting pH of the solution A, wherein a mass concentration of the second pectin gel is 2-5%, the pH of the solution A is 8-12, and an esterification degree of the first pectin gel is higher than an esterification degree of the second pectin gel; preparing a calcium salt solution having a $Ca^{2+}$ concentration of 1-5 mmol/L to obtain a solution B; and
   (7) infiltrating the dried pectin gel in the solution B, transferring the dried pectin gel to the solution A, and then transferring the dried pectin gel from the solution A to the solution B.

2. The method according to claim 1, wherein: the esterification degree of the first pectin gel is 50-80%.

3. The method according to claim 1, wherein: the soluble solid comprises at least one of sucrose, fructose, or glucose.

4. The method according to claim 1, wherein: the load comprises at least one of high molecular substances or low molecular substances, wherein the high molecular substances comprise at least one of microorganisms, enzymes, or proteins, and a molecular weight of the low molecular substances is less than a molecular weight of the high molecular substances.

5. The method according to claim 4, wherein:
   in step 4:
      when the load is the low molecular substances, using ultra-high pressure homogenization to obtain the formed pectin gel; and
      when the load is the at least one of microorganisms, enzymes, or proteins, directly pouring the mixture into the mold to obtain the formed pectin gel.

6. The method according to claim 1, wherein: a temperature in the steps (4) and (5) is a temperature for maintaining an activity of the load.

7. The method according to claim 1, wherein: the esterification degree of the second pectin gel is 10-30%.

8. The method according to claim 1, wherein step (7) comprises:
   repeatedly infiltrating the dried pectin gel in the solution B, transferring the dried pectin gel to the solution A, and then transferring the dried pectin gel from the solution A to the solution B for 1-2 times.

9. The method according to claim 1, wherein the pouring the mixture into the mold to obtain the formed pectin gel comprises pouring the mixture into a second package, hermetically packaging in vacuum, placing the mixture after the hermetically packaging in a second pressure vessel filled with the pressure transmitting liquid, treating at a pressure of 400-600 MPa for 5-30 minutes, pouring the mixture into the mold, and leaving to stand for 1-3 days to obtain the formed pectin gel.

10. The method according to claim 1, wherein the pouring the mixture into the mold to obtain the formed pectin gel comprises directly pouring the mixture in step (3) into the mold to obtain the formed pectin gel.

* * * * *